US008457982B1

(12) United States Patent
Brophy

(10) Patent No.: US 8,457,982 B1
(45) Date of Patent: Jun. 4, 2013

(54) METHOD OF LIMITING INSURER EXPOSURE TO RENAL DIALYSIS CLAIMS LIABILITY

(75) Inventor: John Brophy, Phoenixville, PA (US)

(73) Assignee: Kimberton Healthcare Consulting, Inc., Phoenixville, PA (US)

( * ) Notice: Subject to any disclaimer, the term of this patent is extended or adjusted under 35 U.S.C. 154(b) by 551 days.

(21) Appl. No.: 12/397,962

(22) Filed: Mar. 4, 2009

Related U.S. Application Data

(60) Provisional application No. 61/069,838, filed on Mar. 18, 2008.

(51) Int. Cl.
*G06Q 10/00* (2006.01)
*G06Q 50/00* (2006.01)

(52) U.S. Cl.
USPC .................................. 705/2; 705/3

(58) Field of Classification Search
USPC .......................................... 705/2–4
See application file for complete search history.

(56) References Cited

U.S. PATENT DOCUMENTS

| 7,260,548 | B1* | 8/2007 | Allsup | 705/4 |
| 2007/0271119 | A1* | 11/2007 | Boerger et al. | 705/2 |

OTHER PUBLICATIONS

The organization and financing of kidney dialysis and transplant care in the United States of America. Richard A Hirth. International Journal of Health Care Finance and Economics. Dordrecht: Dec. 2007. vol. 7, Iss. 4, p. 301-18 (18 pp.).*
Risk-Adjustment system for the Medicare Capitated ESRD Program. Jesse M Levy, John Robst, Melvin J Inger. Health Care Financing Review. Washington: Summer 2006. vol. 27, Iss. 4, p. 53-69 (13 pp.).*
Crider, Inc. Employee Benefit Program, Crider, Inc. Plant Employee Benefit Program, Plan Amendment, p. 1 (Feb. 1, 2008).

* cited by examiner

*Primary Examiner* — Robert Morgan
*Assistant Examiner* — Kristine Rapillo
(74) *Attorney, Agent, or Firm* — Volpe and Koenig, P.C.

(57) ABSTRACT

Systems and methods are provided to limit exposure of medical Plans to high liabilities for renal dialysis without exposing the insured patient to out-of-pocket liability while still allowing the patient to receive dialysis as they need it. In one embodiment, this goal is achieved by providing an ERISA medical insurance Plan structure that limits Plan responsibility to 125% of the Medicare approved amount for the services provided, and simultaneously supplements coverage of the patient under Medicare Part B. Because Medicare regulations prohibit providers from balance-billing patients subsequent to billing Medicare, the patient cannot be billed for amounts in excess of the Plan limits.

15 Claims, 2 Drawing Sheets

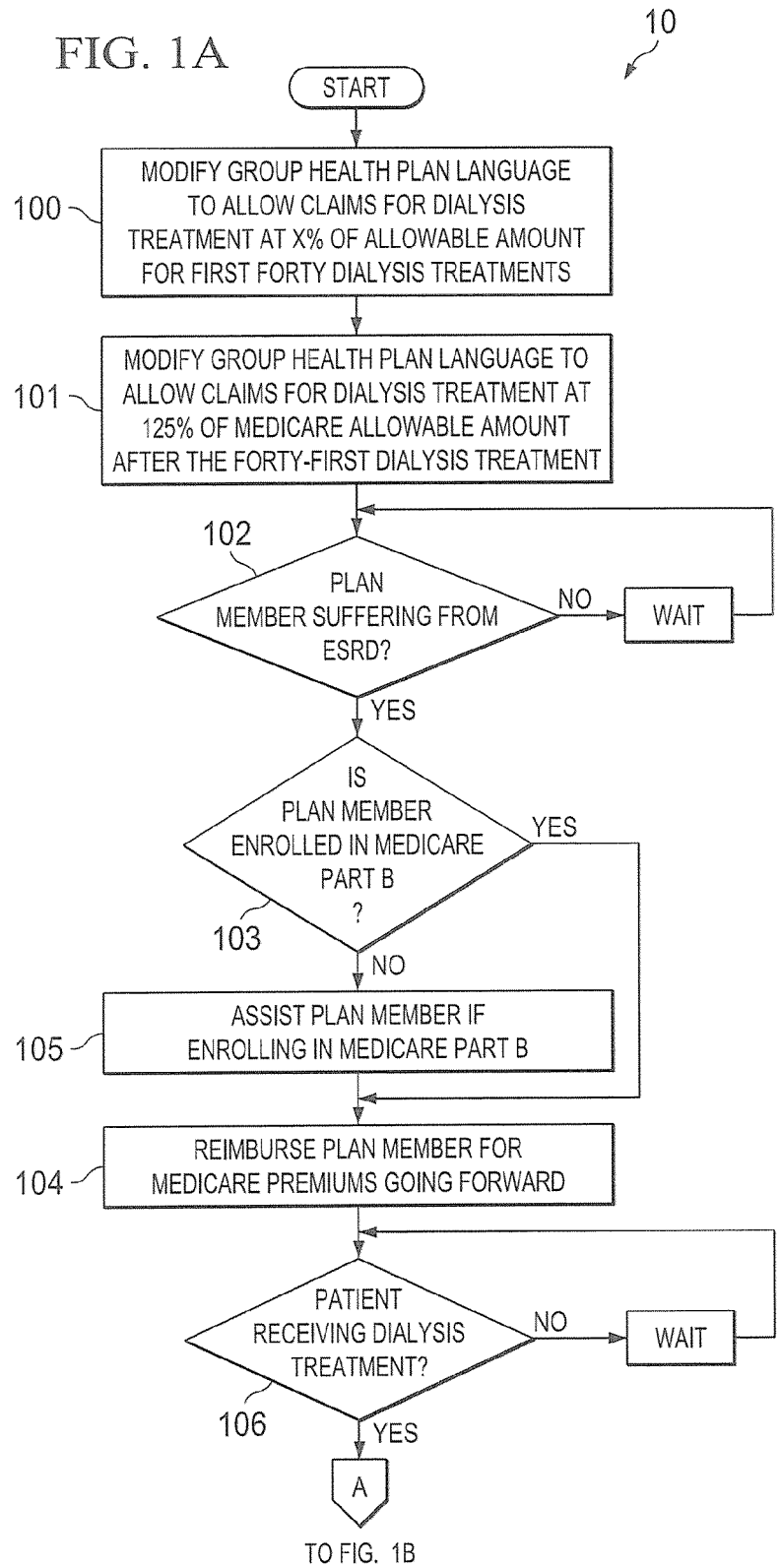

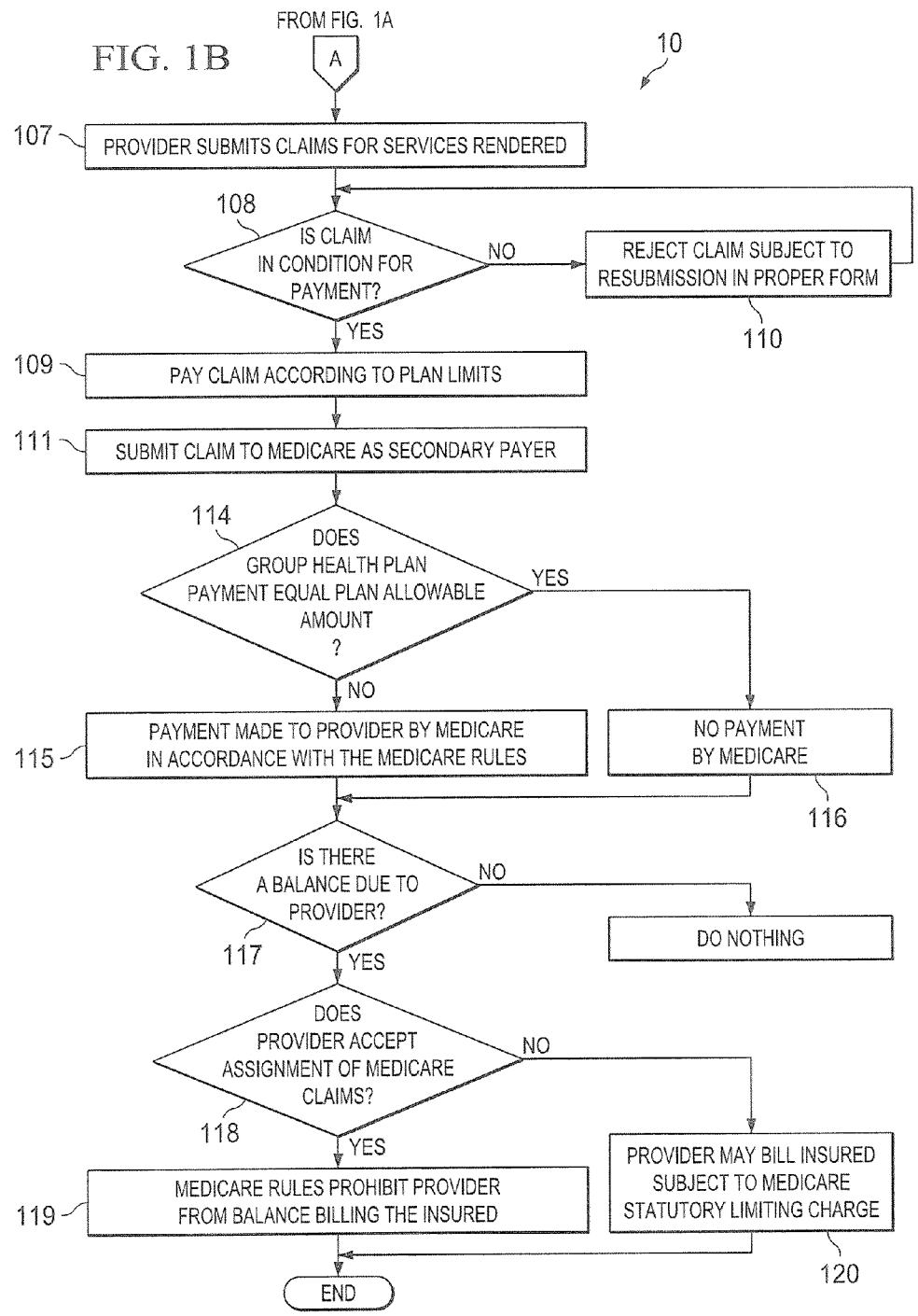

METHOD OF LIMITING INSURER EXPOSURE TO RENAL DIALYSIS CLAIMS LIABILITY

CROSS-REFERENCE TO RELATED APPLICATIONS

This application claims priority to U.S. Provisional Patent Application No. 61/069,838 filed Mar. 18, 2008, entitled METHOD OF LIMITING INSURER EXPOSURE TO ESRD CLAIMS LIABILITY, the disclosure of which is hereby incorporated by reference in its entirety.

TECHNICAL FIELD

The present disclosure relates to risk management and allocation by medical Plans. More particularly, the present invention relates to systems and methods for providing such medical Plans with a mechanism to limit exposure to high renal dialysis liabilities without depriving their insured members of the life extending kidney dialysis they need, or exposing those members to out-of-pocket liability.

BACKGROUND OF THE INVENTION

Chronic kidney disease is a progressive loss of renal function over a period of months or years most often due to diabetic nephropathy, hypertension, glomerulonephritis or other causes. The disease is tracked by doctors through five stages. Each stage is a progression through an abnormally low and progressively worsening glomerular filtration rate. Stage 1 is mildly diminished renal function, with few overt symptoms. Stage 5 is a severe illness characterized by essentially total kidney failure and requiring some form of renal replacement therapy (dialysis or renal transplant). Stage 5 is also referred to as end-stage renal disease (ESRD) by the U.S. Centers for Medicare and Medicaid Services and U.S. federal legislation regarding the issue.

Patients suffering from ESRD require some from of renal replacement therapy, generally either regular dialysis or a kidney transplant. Approximately 17,100 kidney transplants were performed in the United States in 2006. However, at the same time, approximately 74,000 individuals were awaiting a donor kidney. Individuals awaiting a donor kidney must regularly undergo dialysis to maintain their body's internal equilibrium of water and minerals (such as sodium, potassium, chloride, calcium, phosphorus, magnesium, sulfate) as well as the daily metabolic load of fixed hydrogen ions. This is generally accomplished through thrice weekly hemodialysis or peritoneal dialysis sessions which severely impact patient quality of life.

Dialysis services are generally provided on an outpatient basis at dialysis clinics. The dialysis industry is dominated by two large corporations, Fresenius Medical Care AG (2,388 dialysis clinics in North America, Europe, Latin America and Asia-Pacific as of Dec. 31, 2008) and DaVita, Inc. (1,449 dialysis clinics in the U.S. as of Dec. 31, 2008). The average cost of a single dialysis session among all patients in the United States is approximately $320 dollars. However, this cost is not shared equally among all payers. Larger insurers, such as Aetna, Cigna or any of the various Blue Cross Blue Shield entities, have insured pools large enough to provide the leverage necessary to negotiate reduced fee schedules from dialysis providers. However, individuals and small entities pay, on average, six times the price paid by large risk pools and it is not uncommon for the expense to exceed 15 times the rates paid by the larger pools. Particularly hurt by the imbalance in pricing are self-funded and other medical Plans with one or a few patients suffering from ESRD.

The Medicare approved amount for adult ESRD treatment is currently approximately $245 per dialysis session, of which the government pays 80% and the patient pays 20%. However, due to lack of competition in the marketplace and lack of leverage on the part of most medical Plans, the average provider cost per session for patients covered by such Plans is $1,415. Amounts not covered under the health Plan are potentially billed directly to the dialysis patient who would be responsible to pay out-of-pocket.

Under the Medicare rules, patients suffering from ESRD are generally eligible to enroll in Medicare after three months of treatment, with some patients eligible immediately upon starting treatment. However, Medicare serves as a "secondary payer" for individuals with ESRD who have coverage under a group health Plan during the first 30 months of Medicare entitlement. Thus, the patient's medical Plan is presently the responsible primary payer for dialysis benefits for 33 months before Medicare becomes the primary payer. During this time period the per patient costs to the Plan can exceed $1,000,000.

It would be advantageous for medical Plans to have a mechanism to limit exposure to these high dialysis liabilities without exposing the insured patient to out-of-pocket liability and yet still receive the life extending treatment of kidney dialysis they need.

BRIEF SUMMARY OF THE INVENTION

Systems and methods are provided to limit exposure of medical Plans to high liabilities for certain medical treatments without exposing the insured patient to out-of-pocket liability while still allowing the patient to receive medical treatments as they need them. In one embodiment, the medical treatment is kidney dialysis made necessary because of end-stage renal disease (ESRD). In one embodiment, this goal is achieved by providing a medical insurance Plan structure that limits Plan responsibility to 125% of the Medicare approved amount for the services provided, and simultaneously supplements coverage of the patient under Medicare Part B. Because Medicare regulations prohibit providers from balance-billing patients subsequent to billing Medicare, the patient cannot be billed for amounts in excess of the Plan limits.

Providers submitting claims to a medical Plan protected according to the present invention are paid the lesser of the claimed amount or 125% of the Medicare allowed amount. Providers not receiving full payment must then submit the claim to Medicare for reimbursement. Medicare will allow $0 if the Plan pays 100% of the Plan allowable amount and therefore there is no co-insurance responsibility on behalf of the member. If the Plan provides for a member co-insurance amount of greater than 0%, then the amount allowed by Medicare will be an amount less than what Medicare would have paid had the combination of benefit instruments not been implemented. Medicare participating providers and providers accepting assignment of Medicare claims will be prohibited from balance billing the patient directly for additional compensation. Non-participating providers not accepting assignment of Medicare claims will be limited to billing the patient the statutory limiting charge less any amounts paid by the health Plan or by Medicare.

The medical service provider receives payment for the service rendered in an amount in excess of that allowed by Medicare while the patient is insulated from excess out-of-pocket co-insurance payments by confluence of the balance billing rules of the Medicare system and the new Plan benefit that reimburses ESRA members the cost of their Part B premium. Additionally, all Plan members benefit from lower premiums through reduced overall costs to the Plan, and the Medicare program will benefit from a lower secondary payment responsibility in cases where the primary payer coinsurance responsibility is less than 100%.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIGS. 1A and 1B are flow diagrams of one embodiment of a method of implementing a medical benefit Plan that is described by the present invention.

DETAILED DESCRIPTION OF THE INVENTION

FIGS. 1A and 1B are flow diagrams of one embodiment 10 of a method of implementing a medical benefit Plan that is described by the present invention. In one embodiment, the medical Plan is an Employees Retirement Income Security Act (ERISA) sponsored welfare benefit plan (Plan), but the invention could cover any type of medical Plan that provides benefits of the type discussed herein. These Plans may include medical, ERISA, health, etc. The method of FIGS. 1A and 1B could, for example, be used in one or more general purpose computers under control by one or more software coded applications.

The method shown in FIGS. 1A and 1B may be implemented into an existing ERISA-sponsored welfare benefit Plan (or into another similar Plan) by modifying that Plan (as discussed below), or may be implemented directly in any new Plan. In either case, the existing or new ERISA Plan will be set forth in a Plan document similar to a traditional group health insurance policy. In one embodiment, the ERISA Plan is a self-funded Plan wherein an employer assumes the direct risk for payment of claims and benefits to employees as opposed to shifting that risk to a third-party underwriter or insurer. The present invention may be practiced irrespective of whether the self-funded Plan secures, as is common practice, "stop/loss" insurance that protects the health Plan from claim costs above a specified contractual amount. For example, a self-funded ERISA Plan may purchase stop/loss coverage above $100,000 per member per year. Under this coverage, the health Plan pays claim costs up to $100,000 and the stop/loss insurer pays costs in excess of $100,000. Self-funded health Plans pay premium payments to the stop/loss insurer, typically on a per member per month basis, for such protection.

In process 100, the existing ERISA Plan is identified and modified (as will be discussed herein) to provide that, for all Plan members, claims for the first forty dialysis treatments will be paid in accordance with the Plan's current benefit. Forty treatments assumes a treatment once every three weeks for thirty months and can be adjusted as desired by the Plan administrator.

In process 101, the health Plan of process 100 is further modified to provide that after the initial forty dialysis treatments for a given Plan member, reimbursement for each subsequent dialysis treatment session will be paid at an indexed amount calculated to exceed the "Medicare allowable amount" (in this example 125% of the Medicare allowable amount). The Medicare allowable amount is determined by The Centers for Medicare and Medicaid (CMS) regulation.

Process 102 then determines if any Plan member is diagnosed with ESRD. This can be accomplished, for example, by searching a database (not shown) using an application program running on a computer or other processor. If no such member is identified, no action is taken until such time as a Plan member is diagnosed with stage 5 renal failure requiring dialysis. When a Plan member is diagnosed with ESRD or an individual becomes a member of the Plan who already suffers from ESRD, process 103 determines whether the Plan member is already enrolled in Medicare Part B on some eligibility grounds. If the Plan member is not so enrolled, but is entitled, then process 105 assists the Plan member in obtaining Medicare Part B coverage since at this point the Plan member is statutorily entitled to so enroll as a result of the Plan member's ESRD diagnosis. All of these actions are accomplished, for example, using processors to track the necessary information for enrollment and for determining, perhaps based upon a computer analysis of Plan members medical payments, which Plan members have been diagnosed with ESRD.

Process 104 begins to reimburse members for their Medicare Part B premium on a going forward basis. Such reimbursement continues as long as the member remains in the Plan, and is enrolled in Medicare Part B and receives dialysis treatment for ESRD, subject to any annual or lifetime maximum restrictions defined in the Plan.

Process 106 determines whether the patient is currently receiving dialysis treatment. If no treatment is being received, no action is taken until dialysis treatments begin. Upon delivery of dialysis treatment by a Plan member, the provider, under control of process 107, submits a claim for payment for the dialysis treatment provided.

Process 108 determines if the claim is in proper form to be considered. If not, the claim is rejected and returned to the provider subject to resubmission in proper form under control of process 110. Upon submission of a claim in proper form, process 109 pays the claim subject to the "Maximum Allowable Benefit" Plan limitations. A provider who is not paid the full amount may then bill the patient prior to the time when the patient is covered by Medicare, i.e., in the first 3 months.

Upon payment to the provider by the Plan on the claim submitted at process 108, the claim is subsequently submitted by the provider to Medicare as a secondary payer at process 111. Typically, the amount already paid by the Plan will exceed the maximum amount allowed by Medicare if Medicare was the primary payer. In accordance with the present invention, this is the case after the 40$^{th}$ dialysis treatment as the Plan allowable amount is indexed to exceed the Medicare allowable amount (here by 25%). Note that the Plan can determine whether to use 25% or any other percentage. The reason for paying greater than the Medicare amount is because if the Plan paid less than Medicare, the member's responsibility (i.e., co-insurance) would increase, making the member worse off. This could call into question the sufficiency of the Plan's primary payment with respect to the Medicare Secondary Payer statute.

Under current Medicare regulations, Medicare will allow $0 if the Plan pays 100% of the allowable amount, and therefore there is no coinsurance responsibility on behalf of the member. If the Plan provides for a member coinsurance amount of greater than 0%, then the amount allowed by Medicare will be an amount less than what Medicare would have paid had the combination of benefit instruments not been implemented as controlled by processes 114 and 116.

If the amount paid by the Plan is less than the amount allowed by the Plan, Medicare Part B will pay up to 80% of the Medicare allowable amount, in accordance with the Medicare rules and as seen by process 115.

Process 117 determines if a balance is due to the provider because of an underpayment by the Plan in combination with Medicare. If there still remains a balance unpaid to the provider, process 118 determines whether the provider is a Medicare participant or has accepted Medicare assignment in this instance. Providers who accept Medicare patients are reimbursed up to the current Medicare allowable amount for all covered services, and CMS regulations state that the Medicare allowable amount is considered payment in full as controlled by process 119. Providers may only collect any applicable cost sharing (i.e., co-insurance) amounts from the Plan member, and may not otherwise charge or balance bill the member. Consequently, if the provider is a Medicare participant or has accepted Medicare assignment they have effectively agreed to accept the Medicare allowable amount for the service and are prohibited by regulation from balance billing the patient any remaining balance for the dialysis treatment.

If the provider has not agreed to accept assignment of Medicare claims, the provider can then bill the patient for the balance of treatment up to the statutory limiting charge, as shown at process 120, which is 115% of the Medicare allowable amount for non-participating providers. Since the Plan allowable amount is indexed to exceed the Medicare allowable amount (here by 25%), the member will not be subject to balance-billing with non-participating providers either.

It should now be apparent that the above-described method provides ERISA sponsored welfare benefit Plans with a mechanism to limit exposure to dialysis for kidney failure without depriving their insured employees of the life extending kidney dialysis they need, or exposing said employees to out-of-pocket balance-billing liability. The present invention also contemplates a method by which the method of limiting insurer exposure to ESRD claims liability is administered via a third-party administrator that actively implements all necessary Plan document language modifications for their clients and assists with acquiring Medicare Part B coverage for their client's employees/members having ESRD. This will allow further collective bargaining economies and will transfer the pricing leverage from the providers to the group health Plan.

The following language is one example of language which should be in any Plan that wishes to take advantage of the concepts discussed herein. This language could be added as a modification to existing Plans or as part of the language of a new Plan. For other medical treatments, other similar language would be used.

Outpatient Renal Dialysis Services

The member's first forty renal dialysis visits, cumulative and not subject to annual reset, are paid at XX % (insert Plan desired amount—e.g. 70% or 80%, etc.) of the allowable amount. Additional visits are paid at 125% of the Medicare allowable amount.

Medicare Part B Reimbursement

If you or your covered dependent has End-Stage Renal Disease ("ESRD"), the Plan's medical programs primary status applies during the first 30 months of dialysis, or the first 30 months of treatment in connection with a transplant. Thereafter, Medicare generally become the primary payer of benefits.

The Medicare Secondary Payer statute requires the Plan to identify members in the Plan, including eligible dependents, who are eligible for Medicare, including those eligible based on ESRD. To ensure the correct coordination of claims payments, members are required to provide the Plan the basis for their eligibility to Medicare (age, ESRD, or disability) and the effective date of Medicare Part A and Part B.

During this period where the Plan has primary status, Medicare Part B monthly premiums for covered members and their dependents that have become entitled, including dually entitled, to Medicare based on ESRD, will be covered by the Plan. Reimbursement for monies withheld by Medicare from Social Security, Railroad Retirement, or Office of Personnel Management payments will be made at the end of each calendar quarter.

While the concepts discussed herein are described with respect to renal disease, the concepts can be used to limit liability for any number of other diseases, providing they each fit the reimbursement parameters described herein for renal disease. Such reimbursement can be by Medicare, Medicaid or any other form of reimbursement mandated by binding governmental authority on providers. Note also that while Medicare and/or Medicaid is government run, the secondary payer could be a private company or association so long as it has a mandated upper payment limit.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for limiting exposure to liabilities in a private medical benefit Plan arising from a need for a specific medical treatment, said method comprising:

modifying a criteria of said private medical benefit Plan using a processor to limit payment on behalf of a patient to a provider for said medical specific treatment to a patient for an initial number N of treatments to a predetermined percentage Y % of the private medical benefit Plan's allowable amount for said specific treatment;

modifying the criteria of said private medical benefit Plan using a processor to limit payment on behalf of said patient to a provider for providing said patient with said specific treatment in excess of N treatments to an amount which is X % above a Medicare allowable amount for said specific treatment;

if said provider accepts assignment of claims from a government sponsored secondary coverage payer, causing said provider to exclusively submit any underpayment of said provider's charges to said government sponsored secondary coverage payer responsible for said patient; and if said provider does not accept assignment of claims, causing said provider to limit any amount billed to said patient to a maximum amount set by a controlling authority.

2. The method of claim 1 wherein said private medical benefit Plan may assist said patient in obtaining said secondary coverage by a government sponsored secondary coverage payer.

3. The method of claim 2 wherein said secondary coverage payer is Medicare Part B.

4. The method of claim 1 wherein said secondary coverage payer is Medicare Part B.

5. The method of claim 4 wherein said specific medical treatment is renal dialysis maintenance services.

6. The method of claim 1 wherein said Medicare allowable amount comprises a Maximum Allowable Benefit under Medicare Part B.

7. The method of claim 1 wherein said controlling authority comprises The Centers for Medicare and Medicaid Services (CMS) regulation.

8. The method of claim 7 further comprising:
determining if any private medical benefit Plan members are diagnosed with ESRD and whether any such diagnosed private medical benefit Plan members are already enrolled in Medicare Part B; and
if any such members are not so enrolled, assisting said unenrolled members to become so enrolled, as necessary.

9. A method for limiting exposure to maintenance dialysis services in a private medical Plan comprising:
modifying a criteria of said private medical Plan using a processor to have a provision that claims for dialysis treatments for all private medical Plan members will be paid in accordance with the private medical Plan's current benefit;
modifying the criteria of said private medical Plan to have a provision that for all private medical Plan member's claims for dialysis treatments after an initial number of treatments N will be paid at a predetermined percentage Y % of the Medicare allowable amount, where Y % exceeds 100%;
determining if any private medical Plan member is diagnosed with ESRD;
determining if any ESRD-diagnosed private medical Plan member is already enrolled in Medicare Part B;
assisting any ERSD-diagnosed private medical Plan member determined not to be so enrolled to enroll in Medicare Part B, as necessary;
upon receipt of a provider claim for payment for rendering maintenance dialysis services to a private medical Plan member, reimbursing said provider up to a fixed limit set by the private medical Plan for each said claim from 1 to N claims; and
upon receipt of a claim from a Medicare participating provider for payment for rendering maintenance dialysis services to private medical Plan members, reimbursing said provider said Y % for each claim greater than N, whereby when said claim is submitted by said provider to Medicare as a secondary payer, said provider will not be able to balance-bill said private medical Plan member.

10. The method of claim 9 wherein said Medicare allowable amount comprises a Maximum Allowable Benefit under Medicare Part B.

11. A method for administering medical benefit Plans, said method comprising:
determining if a private medical Plan member has a particular medical condition;
using a computer controlled processor to enroll any said determined private medical Plan member in a government controlled third-party payer Plan according to the rules of said third-party payer Plan, said enrollment entitling said private medical Plan member to use said third-party payer in a secondary capacity to said private medical Plan for said particular medical condition, subject to any coordination of benefits period statutorily imposed by said third-party payer Plan;
paying to a provider of certain medical services to said private medical Plan member a private medical Plan determined amount for a certain number N of certain medical services;
using a computer controlled processor to modify said private medical Plan to limit payment on behalf of said private medical Plan member to a provider of certain medical services for providing said private medical Plan member with said certain medical services in excess of N services to an amount that exceeds by a certain pre-established amount a maximum payment amount for said certain medical services in excess of N, said maximum payment amount is set by Medicare; and
paying to a provider of said certain medical services to said private medical Plan member the amount that exceeds by a certain pre-established amount the maximum payment amount for said certain medical services in excess of N.

12. The method of claim 11 wherein said third-party Plan is Medicare Part B.

13. The method of claim 12 wherein said medical condition requires maintenance renal dialysis.

14. The method of claim 12 wherein said number N is a number approximating a waiting period established under Medicare.

15. The method of claim 11 wherein said maximum payment amount comprises a Maximum Allowable Benefit under Medicare Part B.

* * * * *

UNITED STATES PATENT AND TRADEMARK OFFICE
CERTIFICATE OF CORRECTION

PATENT NO. : 8,457,982 B1  
APPLICATION NO. : 12/397962  
DATED : June 4, 2013  
INVENTOR(S) : John Brophy Page 1 of 1

It is certified that error appears in the above-identified patent and that said Letters Patent is hereby corrected as shown below:

IN THE SPECIFICATION

In column 1, line 39, delete "from" and insert --form--, therefor.
In column 3, line 1, delete "ESRA" and insert --ESRD--, therefor.

IN THE CLAIMS

In claim 9, at column 7, line 58, delete "ERSD-" and insert --ESRD--, therefor.

Signed and Sealed this
Fifteenth Day of October, 2013

Teresa Stanek Rea
*Deputy Director of the United States Patent and Trademark Office*